United States Patent [19]
Boyd et al.

[11] Patent Number: 5,433,120
[45] Date of Patent: Jul. 18, 1995

[54] SAMPLING SYSTEM FOR SEPTUM CLOSED CONTAINER

[75] Inventors: Charles R. Boyd, Victoria; John D. Anderson, Lake Jackson, both of Tex.

[73] Assignee: Texas Sampling, Inc., Victoria, Tex.

[21] Appl. No.: 100,479

[22] Filed: Jul. 30, 1993

[51] Int. Cl.⁶ .............................................. G01N 1/10
[52] U.S. Cl. ........................... 73/863.81; 73/863.71; 73/864.74; 73/864.86
[58] Field of Search .......... 73/863.81, 863.71, 863.03, 73/863.43, 864.74, 864.86

[56] References Cited

U.S. PATENT DOCUMENTS

| | | | |
|---|---|---|---|
| Re. 34,687 | 8/1994 | Spencer | 73/863.71 |
| 2,693,705 | 11/1954 | Casler et al. | |
| 2,844,964 | 7/1958 | Guibert | |
| 3,083,577 | 4/1963 | Nelson et al. | 73/863.71 |
| 3,103,807 | 9/1963 | Broerman | 73/863.71 |
| 3,383,923 | 5/1968 | Conche et al. | |
| 3,429,186 | 2/1969 | Price et al. | 73/863.71 |
| 3,438,263 | 4/1969 | Webb | |
| 3,575,045 | 4/1971 | Knights | 73/797 |
| 3,719,086 | 3/1973 | Bannister et al. | |
| 3,872,730 | 3/1975 | Ringrose et al. | |
| 3,985,016 | 10/1976 | Haruki | 73/864.86 |
| 4,014,216 | 3/1977 | Thornton et al. | |
| 4,163,392 | 8/1979 | Fleenor et al. | 73/864.35 |
| 4,199,988 | 4/1980 | Riegger | 73/863.81 |
| 4,230,665 | 10/1980 | Huber | 73/863.21 X |
| 4,252,021 | 2/1981 | Drushel | |
| 4,270,381 | 6/1981 | DeMaray | 73/19.1 |
| 4,380,176 | 4/1983 | Bauer et al. | |
| 4,580,452 | 4/1986 | Masson | |
| 4,712,434 | 12/1987 | Herwig et al. | 73/863.71 X |
| 4,811,607 | 3/1989 | Walters et al. | 73/861.53 |
| 4,938,381 | 7/1990 | Mandeville et al. | 222/1 |
| 4,986,138 | 1/1991 | Spencer | |
| 4,987,785 | 1/1991 | Spencer | |
| 5,116,330 | 5/1992 | Spencer | 73/863.71 |
| 5,131,282 | 7/1992 | Kuhner | 73/863.71 |
| 5,251,495 | 10/1993 | Kuhner | 73/863.71 |
| 5,265,483 | 11/1993 | Farrell et al. | 73/863.81 X |

FOREIGN PATENT DOCUMENTS

| | | | |
|---|---|---|---|
| 2907558 | 8/1980 | Germany | |
| 11525 | 7/1992 | WIPO | 73/863.71 |

*Primary Examiner*—Hezron E. Williams
*Assistant Examiner*—Daniel Larkin
*Attorney, Agent, or Firm*—Pravel, Hewitt, Kimball & Krieger

[57] ABSTRACT

This invention relates to a sampling system for collecting a sample in a septum closed container. It provides for a reservoir of a predetermined volume which captures a sample and it further provides for routing of the captured sample from the reservoir to the septum closed container.

15 Claims, 4 Drawing Sheets

SAMPLING SYSTEM FOR SEPTUM CLOSED CONTAINER

BACKGROUND OF THE INVENTION

1. Field of the Invention

This invention relates to a sampling system for collecting a sample in a septum closed container. More particularly, this system provides a reservoir of a predetermined volume which, upon actuation of valves on the inlet and outlet of the reservoir, captures a sample and provides for routing of the captured sample from the reservoir to the septum closed container.

2. Description of the Related Art

In the operation of many chemical and other processes, it is often necessary to periodically sample fluids which are flowing within the process at various points. For a variety of reasons, it is often advantageous to collect the fluid in a septum closed container, e.g., the sample is volatile, the fluid presents a safety hazard if released to the atmosphere, or the sample may be sensitive to absorption of air or atmospheric moisture. Several various designs of septum closed containers and samplers are known. Examples of such septum closed containers and samplers are shown in U.S. Pat. Nos. 4,174,632 and 4,887,472 to Jansen and U.S. Pat. Nos. 4,651,574, 4,791,821, 4,879,915 and 4,986,138 to Spencer.

The systems for collecting a sample with the known septum closed containers and samplers present several disadvantages. First, known samplers and associated systems for collecting a sample may contain a "dead volume" i.e., a configuration which allows fluid from a previous sample to occupy a part of the system or sampler and to contaminate a later sample, leading to inaccurate analysis. Also, known systems for the collection of a sample typically require the operation of several valves. This may lead to error in collecting a representative and consistent sample and is time consuming as it requires special procedures. Here, the technician (person catching sample) must allow fluid to flow through the sample line adjacent the septum closed container. Then, he must open the valve to the septum closed container which again presents several disadvantages. Here, the technician must attempt to fill the septum closed container by opening and closing its inlet valve. This leads to a sample which is not of a consistent volume with previous samples, which may make it difficult for laboratory personnel to effectively manage the samples of varying volume. Also, the technician may have a difficult time in filling the septum closed container without overfilling the container. This is especially a problem with small sample containers. Further, in catching a sample in this manner, the septum closed container is usually subjected to process pressure. If process pressure is unexpectedly high, it may cause the overpressuring and subsequent rupture of the septum closed container. This presents a significant safety hazard in that the person catching the sample may be subjected to harmful vapors or fragmented glass or metal portions of the septum closed container.

U.S. Pat. No. 4,987,785 to Spencer discloses a sampling system which provides for constant volume sampling and includes a section of tubing having a predetermined volume with three-way valves on the ends of the tubing. The system provides for the simultaneous operation of the two three-way valves. While this patent addresses several of the disadvantages presented above, it has several shortcomings which significantly limit its usefulness. First, this patent discloses a chain and sprocket system for simultaneous movement of the two three-way valves. This chain and sprocket system would not function effectively in a chemical plant or refinery environment because the chain and sprocket system would need constant adjustment and maintenance to ensure that the valves are moved simultaneously. Also, this chain and sprocket system could easily "freeze-up" due to the corrosive nature of these plant environments. Thus, this system would not be viewed as reliable by personnel operating a chemical plant or refinery. Also, the configuration of the sample system would allow sample fluid to leak into the pressurized gas line used for transferring the sample fluid from the tubing to the sample container and lead to contamination of the next sample or varying sample volumes. Further, this system does not provide for ease of operation, i.e., it does not provide the person catching the sample with assurance that the system is functioning properly. Still further, this system does not provide adequate safeguards against equipment or system failures which are required in a chemical plant or refinery environment.

There exists a need for a sampling system for collecting a sample in a septum closed container which prevents contamination of a sample by fluid from an earlier sample contained in a dead volume, provides a consistent size sample, allows collection of a sample upon the operation of a single valve, is safe to operate in that the sample container is not subjected to process pressure, and which allows samples to be obtained without overfilling the septum closed container.

SUMMARY OF THE INVENTION

The invention relates to a sampling system for collecting a sample in a septum closed container. The system includes a reservoir having a predetermined volume and an inlet and outlet, the inlet and outlet having three-way valves. The valves have dual-action pneumatic actuators for actuating the three-way valves to change the flow through the valves so as to capture a sample in the reservoir. Also, the system includes means for diverting a captured sample from the reservoir to the septum closed container.

With the present invention, the fluid to be sampled normally flows through the reservoir. When it is desired to obtain a sample, the technician activates a single valve which in turn pneumatically actuates the three-way valves to temporarily contain a sample within the reservoir. Then, the system provides for the routing and pressuring of the sample contained in the reservoir from the reservoir to the septum closed container. Further, the pressurized gas purges the system and sampler to remove fluid from any dead volume to ensure that a later sample is not contaminated by fluid from an earlier sample.

The present invention requires a technician to turn only one valve which effects the pneumatic actuation of the three-way valves. The sample is automatically captured in the reservoir and diverted to the septum closed container. This provides for several advantages including a consistent sized sample, easy operation, the avoidance of subjecting the septum closed container to process pressure, and the avoidance of overfilling the septum closed container.

BRIEF DESCRIPTION OF THE DRAWINGS

A better understanding of the present invention can be obtained when the detailed description of exemplary embodiments set forth below is considered in conjunction with the attached drawings, in which.

DETAILED DESCRIPTION OF THE PREFERRED EMBODIMENTS

The present invention relates to a sampling system for collecting a sample in a septum closed container. While this system allows for the collection of a sample in many varieties of septum closed containers, the preferred septum closed container and sampler, which has the needle which passes through the septum, means for venting and purging the sample container and means for holding the sample container are disclosed in commonly owned co-pending applications, U.S. Ser. Nos. 07/795,969, now U.S. Pat. No. 5,301,560 and 08/017,871, hereby incorporated by reference.

Figure 1:
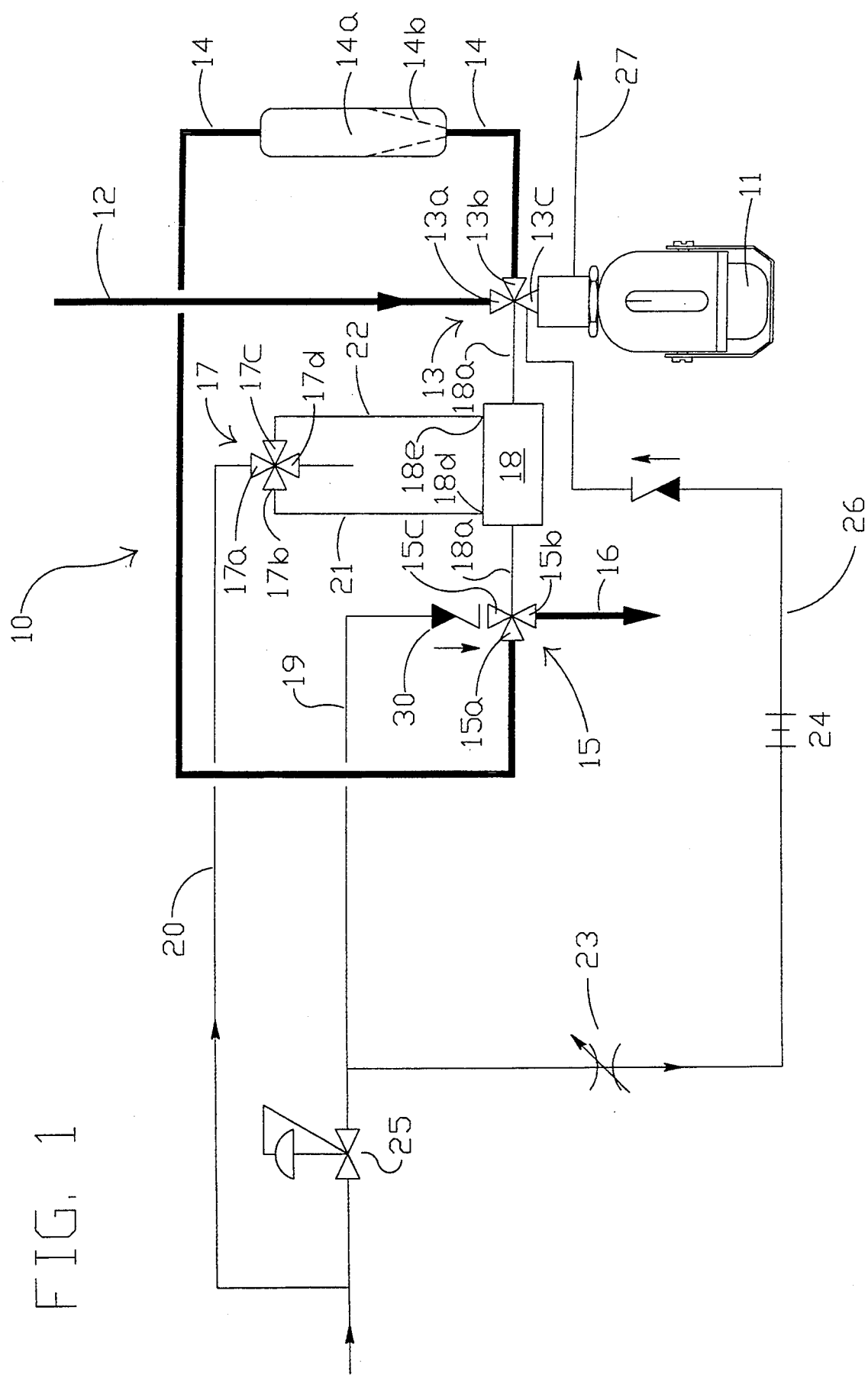
FIG. 1 is a process flow diagram showing an embodiment wherein one actuator operates both three-way valves.

FIG. 1 shows one embodiment of a system 10 for collecting a sample in a septum closed container 11. Under normal operation, i.e., when a sample is not being caught, the fluid flows through sample inlet line 12 and into port 13a of three-way valve 13. As discussed in more detail below, valve 13 is preferably a three-way ball valve which allows for fluid communication between port 13a and port 13b or between port 13b and port 13c as desired. The fluid flows from port 13a, through valve 13 to port 13b, entering line 14. Line 14 combined with sample cylinder 14a, if required, constitutes the "reservoir". The fluid continues through line 14 where it passes through port 15a and port 15b of three-way valve 15. Here, valve 15 is preferably a three-way ball valve similar in design to valve 13. The fluid exits sample outlet line 16. Normally, the fluid flows in the above described path on an ongoing basis. The system, including piping, valves, etc., is configured to avoid any "dead volume" or "pockets", thus ensuring that the sample is representative of the fluid in the process stream. Here, inlet line 12 is connected to the process stream at a location providing a higher pressure than where sample outlet line 16 is connected to the process so as to maintain the flow described above. For example, it is commonly known to provide a sample line from the discharge of a pump to the suction of the pump or from upstream of a control valve to downstream of the control valve. This ensures that a representative sample is continually flowing through the sample line.

When a sample is desired, the technician need only place the septum closed container in its respective holder and activate valve 17. The activation of valve 17 provides a pressurized gas to actuator 18 as described below. Actuator 18 may be any of a variety of known actuators. Preferably, actuator 18 is a 0°–180° dual-action pneumatic actuator. Generally, a dual-action pneumatic actuator has two gas input ports, wherein a pressurized gas supplied through one port moves the actuator from an initial position to a second position and the supply of a pressurized gas to the second gas input port returns the actuator from the second position to the initial position. Actuation of actuator 18 turns stem 18a through a rotation of 180°. This rotation of stem 18a in turn rotates by 180° the balls in three-way valve 13 and three-way valve 15. This rotation of the balls in valve 13 and valve 15 momentarily captures the fluid contained in line 14 and sample cylinder 14a and isolates it from the fluid in inlet line 12 and outlet line 16. This manipulation of valve 13 aligns port 13b with port 13c such that fluid may flow from line 14 and sample cylinder 14a into the septum closed container 11. Manipulation of valve 15 aligns port 15c and port 15a such that a pressurized gas may flow through line 19, into port 15c, out port 15a, and pressure the sample contained in the reservoir, i.e., line 14 and sample cylinder 14a, from the reservoir into the septum closed container 11.

As seen, line 14 and sample cylinder 14a provide a reservoir of constant volume. Here, the volume is predetermined as desired to correspond with the volume of the sample container 11 and meet other considerations such as the requirements of laboratory testing equipment. It is seen that the simultaneous manipulation of valve 13 and valve 15 momentarily captures the fluid to be sampled in the reservoir, line 14 and sample cylinder 14a, and then this captured sample is diverted to the septum closed container 11 and, in fact, is pressured into the septum closed container 11 by the pressurized gas in line 19. The pressurized gas further serves to purge all fluid from the reservoir and the sampler, including the needle, such that these components are cleared of all fluid to avoid the contamination of a later sample. This pressurized gas is vented from the septum closed container 11 via a vent passageway to line 27 to prevent overpressuring the septum closed container 11.

Preferably, the outlet of the sample cylinder 14a includes an interior funnel-shaped section 14b on the outlet of the sample cylinder 14a to the septum closed container 11, such that when the sample is pressured into the septum closed container 11, the liquid is funneled from the cylinder 14a into the container 11 such that no liquid is left in the cylinder 14a. This funnel-shaped section 14b prevents the pressurized gas from blowing through the cylinder 14a, and leaving sample material in the cylinder 14a which may contaminate the next sample taken.

After the sample has been obtained in the septum closed container 11, the technician returns activation valve 17 to its presampling position. As described below, this actuates actuator 18 such that valve 13 and valve 15 are returned to their presampling position, allowing the fluid to flow through the "sample line", consisting of flow through inlet line 12, through port 13a, exiting valve 13 through port 13b, through line 14, through sampler cylinder 14a, continuing through line 14 and exiting through valve 15 and sample outlet line 16. This allows the fluid to flow through the sample line such that the sample line will contain a representative sample for the next sample to be taken.

Figure 2:
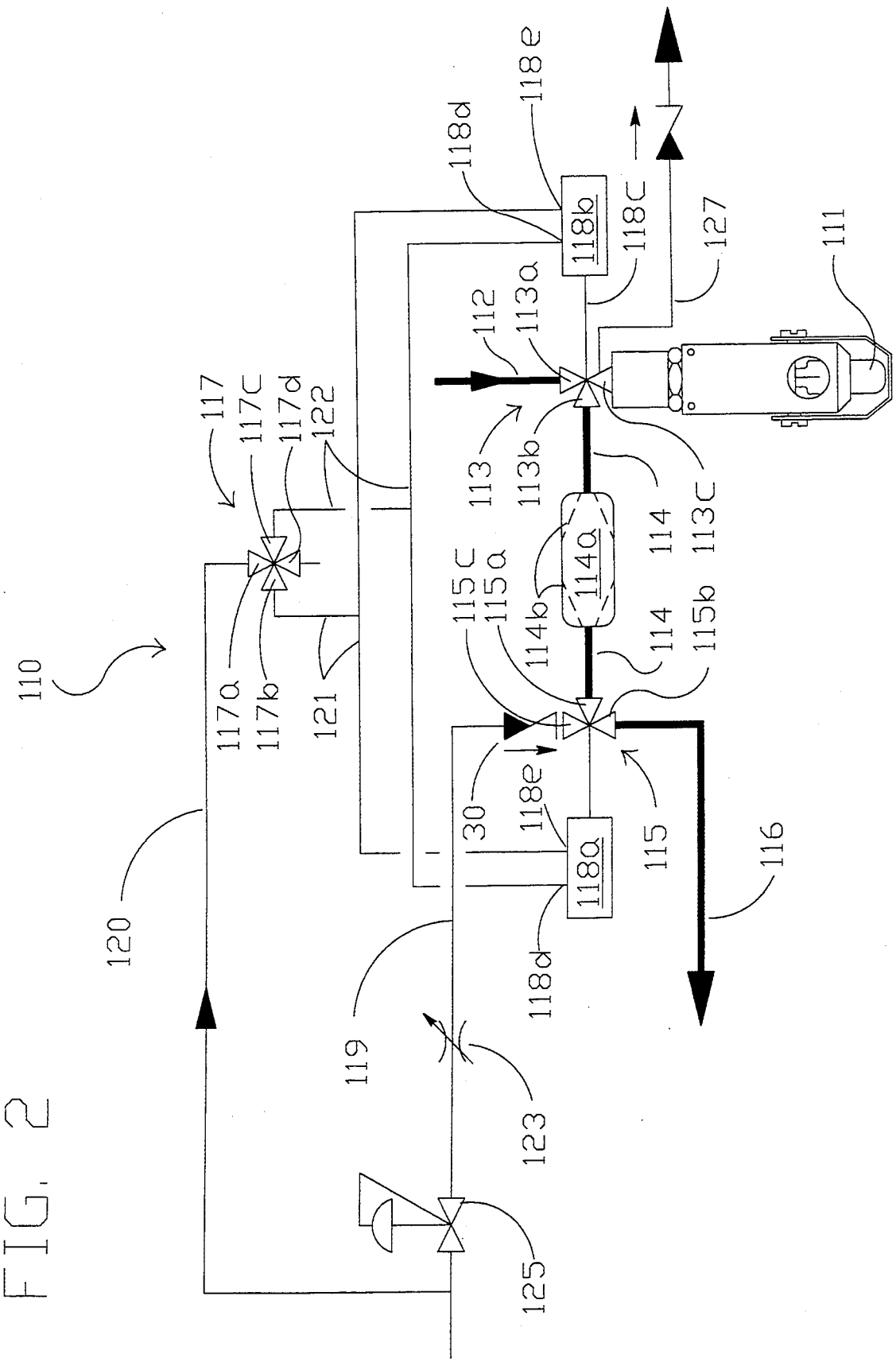
FIG. 2 is a process flow diagram showing an alternate embodiment wherein each three-way valve is actuated by a separate actuator.

FIG. 2 shows an alternate embodiment of a sampling system 110 for collecting a sample in a septum closed container 111. Here, similar components are similarly numbered and function in a similar manner to the embodiment shown in FIG. 1. The embodiment of FIG. 2 is preferred when it is desired to obtain a small sample.

The FIG. 2 system 110 operates in a similar fashion to the FIG. 1 system 10. Under normal operation, when a sample is not being obtained, fluid flows through inlet line 112, through port 113a and port 113b of valve 113, into line 114 and sample cylinder 114a. Fluid flow continues through line 114, through port 115a and port 115b of valve 115, and exits through sample outlet line 116.

The primary difference between the embodiments of FIGS. 1 and 2 involves the predetermined volume contained in the FIG. 1 reservoir (line 14 and sample cylinder 14a) versus the FIG. 2 reservoir (line 114 and sample cylinder 114a). Here, the volume to be contained in the FIG. 2 reservoir is much smaller than that contained in the FIG. 1 reservoir, and hence, in FIG. 2, valve 113 and valve 115 must be physically closer than valve 13 and valve 15 of the FIG. 1 embodiment. This necessitates that valve 113 and valve 115 be actuated by separate actuators 118a, 118b.

Preferably, activation valve 17, 117 is a four-way ball valve having dual flow channels, i.e., two L-shaped channels, with actuators 18,118a, 118b being dual-action actuators. Activation valve 17, 117 is generally the only valve which must be operated by the technician in order to collect a sample in the septum closed container 11, 111. Referring to FIG. 1, upon turning valve 17 from a presample position to a sample position, pressurized gas, for example pressurized air or nitrogen from line 20, enters port 17a and exits port 17b into line 21. This pressurized gas enters a first gas input port 18d and actuates actuator 18, thus moving valves 13 and 15 as previously discussed. Upon actuation, any pressurized gas which exits the actuator 18 flows through line 22, enters port 17c, exits port 17d and is vented to the atmosphere. Likewise, referring to FIG. 2, pressurized gas from line 120 enters port 117a and exits at port 117b, entering line 121. Line 121 is routed to gas input ports 118d on both actuators 118a, 118b providing the pneumatic pressure for actuation. Any pressurized gas which exits the actuators 118a, 118b is routed through line 122 to port 117c, exiting valve 117 at port 117d and venting to the atmosphere.

After the sample is obtained, the technician returns actuation valve 17 to its presample position. In this position, the pressurized gas from line 20, 120 is routed through port 17a, 117a to port 17c, 117c, through line 22, 122, enters the actuator(s) 18, 118a, 118b at a second gas input port 18e, 118e and provides pneumatic pressure to return the actuator(s) 18, 118a, 118b and valves 13, 113, 15, 115 to the presample position. Any pressurized gas which exits the actuators 18, 118a, 118b flows through lines 21, 121, through port 17b, 117b, exiting valve 17,117 through port 17d, 117d, and venting to the atmosphere.

The present inventive system is designed for ease of operation in obtaining a sample. First, to catch a sample one only needs to turn one valve, i.e., activation valve 17,117. This captures the predetermined volume of the sample in the reservoir and automatically diverts this captured sample into the septum closed container 11, 111. Also, a flow indicator, e.g., a rotameter 23,123, may be installed in a pressurized gas stream to assure the technician that the pressurized gas is flowing and that the system is operating correctly. Further, the technician can see the septum closed container filling and is thus assured that the system is operating correctly.

The present inventive system has several advantages over known methods for collecting samples in septum closed containers. First, the inventive systems provide for purging of the reservoir and sampler, including the needle, to prevent fluid from occupying any dead volume to ensure that a later sample is not contaminated by fluid remaining from an earlier sample. The FIG. 1 system 10 contains a continuous purge through line 26 and rotameter 23. Here, the technician may observe rotameter 23 to assure himself that the pressurized gas is continually flowing and that the system is operating correctly. Here, the pressurized gas from line 26 serves to purge the septum closed container 11 of any air or moisture before the sample is taken and purges the fluid from the needle after the sample is taken. The FIG. 2 system 110 provides for purging the needle after the sample is taken such that it will be clean so as to avoid a later sample being contaminated by previous sample material remaining in the needle from the previous sample. Here, after a sample is caught, the technician allows additional gas to flow from line 119, while observing rotameter 123, through the reservoir, to purge the fluid from the sampler, including the needle, such that these components are free of fluid, providing that a subsequent sample is not contaminated. Purging in this manner is particularly applicable when a small sample is to be obtained.

Also, the present system provides for the advantage of consistent size samples. Here, it is preferred that the field technicians, i.e., the operators of the process equipment, work with the laboratory or testing services personnel to determine the specific needs or desires for the size of the sample container and the volume of the sample caught. The laboratory or testing services personnel should consider the equipment which analyzes the sample. For example, an automated gas chromatograph may be designed for operation with a certain sized sample container filled with a certain volume of sample. Here, the inventive sampling system would be designed to fill that container to the predetermined volume such that the same sample container may be used to catch the sample and to automatically analyze the sample in the laboratory. This avoids the errors associated with transferring the sample from one sample container to another sample container for analysis and also requires less manpower.

The inventive sampling system further has the advantage of using the pressurized gas stream, preferably nitrogen from line 19, 119, to push the sample into the sample container 11, 111 rather than relying on process pressure. As shown in FIGS. 1 and 2, a back pressure regulator 25, 125 controls the pressure of the pressurized gas in lines 19 and 119. Here, the back pressure regulator 25, 125 controls the pressure of the gas stream which pushes the captured sample from the reservoir to the septum closed container 11, 111. Preferably, the back pressure regulator 25, 125 would be set at approximately 5 to 10 psig and the pressurized gas would be nitrogen. This 5 to 10 psig of pressure is sufficient to push the sample from the reservoir to the septum closed container 11, 111 while ensuring that the septum closed container is not overpressured. Any excess pressurized gas which flows into the septum closed container 11, 111 is simply vented through vent line 27, 127. Other sampling systems which rely on the process pressure to push the sample into the septum closed container may subject the septum closed container to much higher and unexpected pressure, thus overpressuring and rupturing the septum closed container and possibly injuring the technician due to the release of hazardous sample material or the shattering of the septum closed container.

Preferably, the pressurized gas to valve 15, 115 at port 15c, 115c is provided with a check valve 30, 130, which prevents sample fluid from flowing or otherwise being collected in line 19, 119. Also, preferably line 19, 119 and the check valve 30, 130 are located vertically on top of valve 15, 115 to further prevent sample fluid from moving into line 19,119. Without this check valve 30, 130 and its position on the vertical top of valve 15, 115, sample fluid may enter line 19, 119 so as to vary the amount of sample collected in the septum closed container 11 or contaminate a sample with old sample fluid contained in line 19, 119.

Further, the present system has the advantage of allowing small samples to be caught without overfilling or overflowing the septum closed container 111. This is especially shown in FIG. 2. There, the reservoir, consisting of line 114 and sample cylinder 114a, may be designed for a small volume, e.g., 1 cc, with it being preferred to obtain the 1 cc sample in a 2 cc septum closed container. Thus, the predetermined volume in the reservoir, i.e., 1 cc, halfway fills the 2 cc septum closed container and avoids overfilling. This allows the 2 cc septum closed container to be placed directly on the automatic laboratory analyzing equipment and assures that the automatic analyzer will be presented with a consistently sized sample. Also, this avoids the problem of a laboratory or testing services personnel having to dispose of unneeded, excessive sample material.

The system 10 is also designed to prevent unsafe conditions should the system 10 not function correctly. For example, in the FIG. 1 embodiment, the stem 18a is a contiguous stem (solid stem) through the actuator 18 so as to prevent one valve 13 or 15 from turning without turning the other valve. Also, the system 10 is designed so as to avoid unsafe conditions if valve 13 is operated without a simultaneous operation of valve 15. In the present system 10, unlike the system in U.S. Pat. No. 4,987,785 to Spencer, inlet line 12 is connected to the same three-way valve 13 as is the septum closed container 11. With the present system 10, since port 13a is 180° opposite port 13c and the L-shaped channel 29 (FIG. 3) is at 90°, port 13a cannot be fluidly connected with port 13c so as to overfill the septum closed container 11 with sample fluid from the inlet line 12. Overfilling container 11 may result in overfilling the vent system (not shown) or rupturing the container 11 and overflowing on to the ground. Both of these situations present a significant risk of explosion or exposure to both personnel and equipment.

Figure 3:
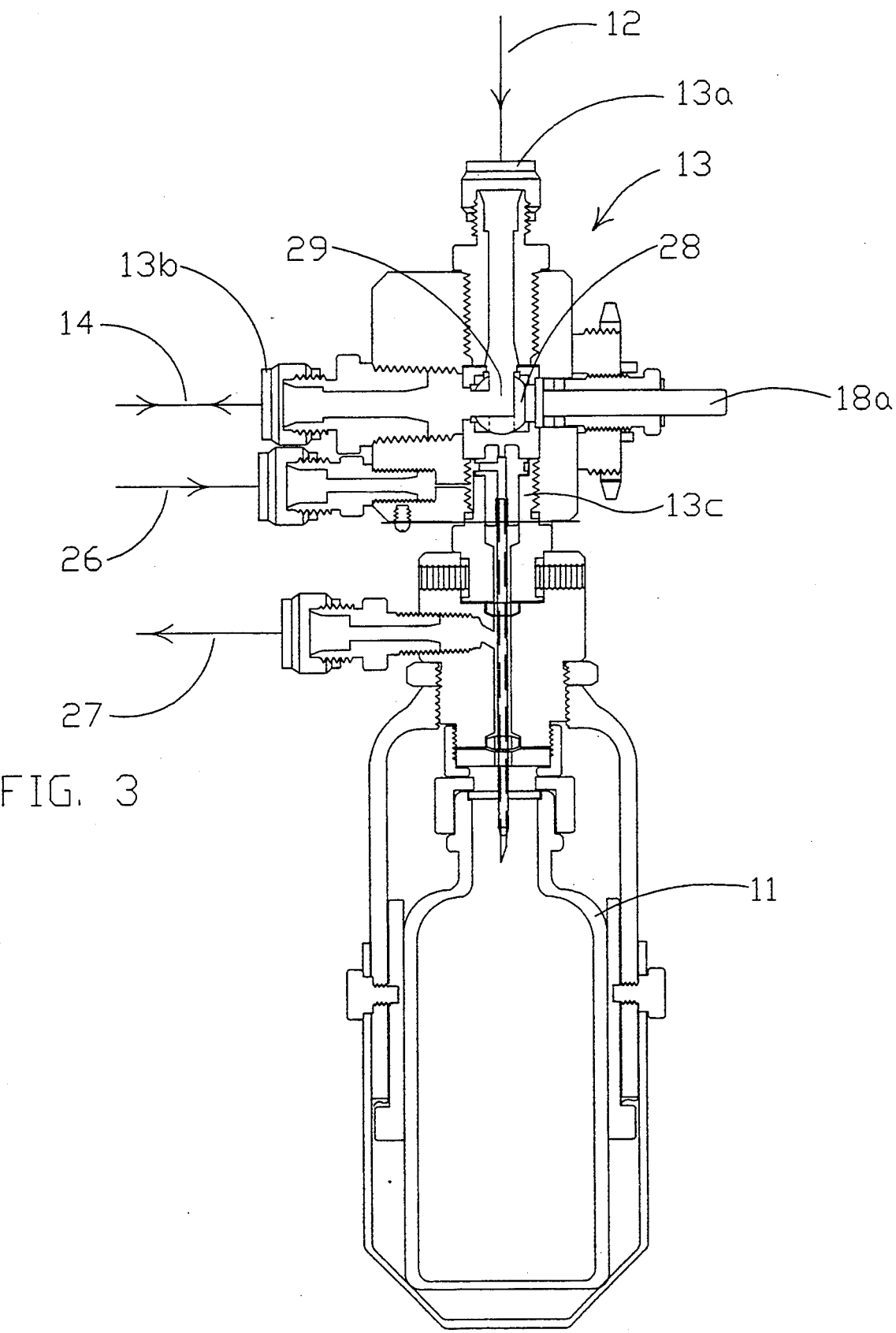
FIG. 3 shows the preferred sampler mechanism and septum closed container of the sampling system embodiment shown in FIG. 1.
Figure 4:
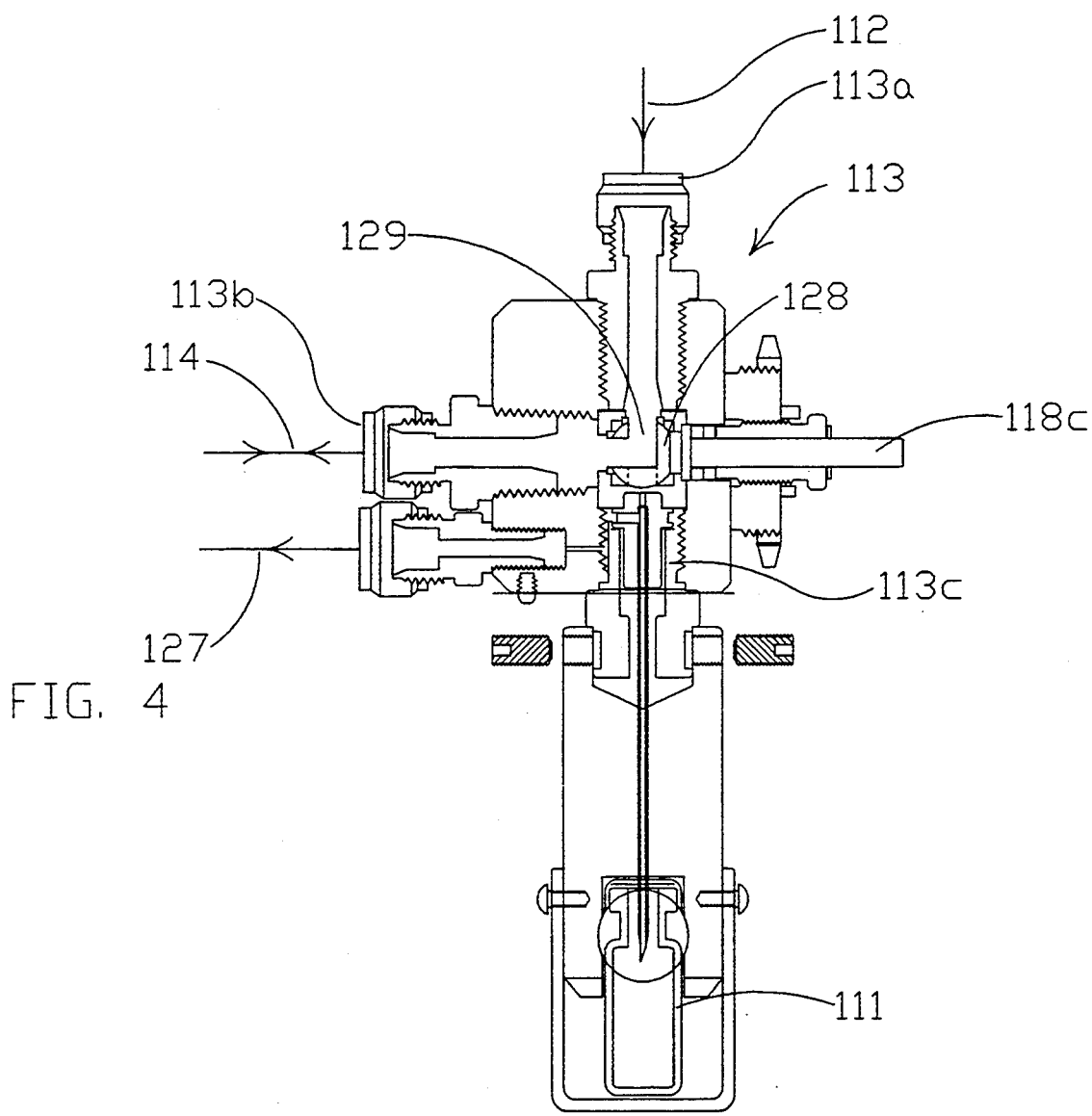
FIG. 4 shows the preferred sampler mechanism and septum closed container of the sampling system embodiment shown in FIG. 2.

FIGS. 3 and 4 show the preferred embodiments of the sampler mechanism and septum closed container of the sampling system embodiments shown in FIGS. 1 and 2, respectively. The details of the sampler mechanism and septum closed containers shown in FIGS. 3 and 4 are included in commonly owned co-pending applications, U.S. Ser. Nos. 07/795,969, now U.S. Pat. No. 5,301,560 and 08/017,871, hereby incorporated by reference. Referring to FIG. 3, the three-way valve 13 has a ball 28 which contains an L-shaped channel 29 and is rotated by stem 18a. When a sample is not being obtained, the fluid flows in line 12, enters port 13a, travels through the L-shaped channel 29 and exits through port 13b into line 14. It can be seen that 180° rotation of ball 28 will align port 13b with port 13c, thereby allowing the sample captured in the reservoir to flow from line 14, through port 13b, through the L-shaped channel 29, through port 13c, and into the septum closed container 11.

The FIGS. 1 and 3 embodiment provides for a purging of the needle by an inert gas, preferably nitrogen, entering through line 26. Purging in this manner accomplishes several functions. First, it provides a clean needle, empty of any sample material, such that the next sample taken will not be contaminated by previous sample material remaining in the needle from the previous sample. Also, purging removes any sample material from the needle which may act to corrode or otherwise plug the needle. Further, purging eliminates moisture and oxygen from the septum closed container 11 which may serve to contaminate fluid contained therein. Purge gas may be supplied continuously to the sampler, the flow rate being controlled by any convenient means such as for example a restriction orifice 24. Any excess purged gas is simply vented through vent line 27.

Referring to FIG. 4, three-way valve 113 is similar to valve 13 of FIGS. 1 and 3. Ball 128 contains an L-shaped channel 129 and is rotated by stem 118c. As shown, when a sample is not being obtained, fluid enters port 113a from line 112, flows through the L-shaped channel 129 and exits through port 113b and line 114. It can be seen that a 180° rotation of ball 128 will align port 113b with port 113c such that sample material may flow from line 114 into the septum closed container 111. This embodiment includes the capability to vent through vent line 127. Venting is needed when excess gas is used to purge the needle after the sample captured in the reservoir is pressured into the septum closed container.

Although the invention has been described with reference to its preferred embodiments, those of skill in the art may from this description appreciate changes and modifications which can be made therein which do not depart from the scope and spirit of the invention as described and claimed hereafter.

What is claimed is:

1. In a sampling system for collecting a sample from a sample line into a septum closed container, the improvement comprising:

a reservoir of predetermined volume integral with the sample line having a first end and a second end, the first end having a first three-way valve and the second end having a second three-way valve, the first and second valves having a first position wherein the sample is allowed to flow through the reservoir and a second position wherein the sample is diverted from the reservoir to the septum closed container;

at least one dual-action pneumatic actuator for simultaneously moving the first valve and the second valve, said actuator having a first gas input port for actuating the actuator to move the first and second valves from the first position to the second position and a second gas input port for actuating the actuator to move the first and second valves from the second position to the first position;

a four-way valve for selectively routing a pressurized gas between the first and second gas input ports to selectively position the first and second valves between the first and the second positions;

means for diverting the captured sample from the reservoir to the septum closed container; and means for preventing overfilling of the septum dosed container upon failure of the first and second valves to move simultaneously.

2. The sampling system of claim 1, wherein the four-way valve is manually operated.

3. The sampling system of claim 1, wherein the means for diverting the sample from the reservoir to the septum closed container comprises means to align a first port of the first three-way valve with the first end of the reservoir and a second port of the first three-way valve with the septum closed container to allow the sample captured in the reservoir to flow into the septum closed container.

4. The sampling system of claim 3, wherein the means for diverting the sample from the reservoir to the septum closed container comprises means to align a first port of the second three-way valve with a supply line of a gas and a second port of the second three-way valve with the second end of the reservoir to allow the gas to push the sample captured in the reservoir into the septum closed container.

5. The sampling system of claim 4, wherein the supply line of gas to the first port of the second three-way valve further comprises means for indicating flow of the gas.

6. The sampling system of claim 5, wherein the means for indicating flow of the gas is a rotameter.

7. The sampling system of claim 4, wherein the first port of the second valve is oriented vertically on top of the second three-way valve.

8. The sampling system of claim 7, wherein the supply line includes a check valve located in proximity to the first port of the second valve to allow the gas to flow in the first port.

9. The sampling system of claim 7, wherein the supply line of a gas includes a back pressure regulator.

10. The sampling system of claim 1, wherein the first end of the reservoir includes an interior funnel-shaped section.

11. The sampling system of claim 1, further comprising means to vent the sample container.

12. The sampling system of claim 1, wherein the sampling system has a needle for penetrating the septum closed container, the improvement further comprising means to purge the needle.

13. The sampling system of claim 1, the improvement comprising wherein the septum closed container has a volume of about 2 cc and the reservoir has a volume of about 1 cc.

14. A method for collecting a sample of a fluid from a sample line into a septum closed container, comprising the steps of:
   allowing the fluid to flow in the sample system, the sample system having:
      a reservoir of predetermined volume having a first end and a second end, the first end having a first three-way valve and the second end having a second three-way valve, the first and second valves having a first position wherein the sample is allowed to flow through the reservoir and a second position wherein the sample is diverted from the reservoir to the septum closed container;
      at least one dual-action pneumatic actuator for simultaneously moving the first valve and the second valve, said actuator having a first gas input port for actuating the actuator to move the first and second valves from the first position to the second position and a second gas input port for actuating the actuator to move the first and second valves from the second position to the first position;
      a four-way valve for selectively routing a pressurized gas between the first and second gas input ports to selectively position the first and second valves between the first and the second positions;
      means for preventing overfilling of the septum closed container upon failure of the first and second valves to move simultaneously;
   manipulating the four-way valve from a first position to a second position to capture the sample in the reservoir, to align the first end of the reservoir containing the captured sample with the septum dosed container, and to align the second end of the reservoir with a source of pressurized gas; and
   manipulating the four-way valve from the second position to the first position to allow the fluid to flow in the sample system.

15. The method of claim 14, wherein the captured sample flows through a needle into the septum dosed container, and further comprising the step of purging the needle.

* * * * *